United States Patent
Hölscher et al.

(10) Patent No.: US 7,141,566 B1
(45) Date of Patent: Nov. 28, 2006

(54) BENZOXAZINE AND BENZOTHIAZINE DERIVATIVES AND THE USE THEREOF IN MEDICAMENTS

(75) Inventors: Peter Hölscher, Berlin (DE); Hartmut Rehwinkel, Berlin (DE); Stefan Jaroch, Berlin (DE); Detlev Sülzle, Berlin (DE); Margrit Hillmann, Berlin (DE); Gerardine Anne Burton, Berlin (DE); Fiona Mcdougall McDonald, Berlin (DE)

(73) Assignee: Schering Aktiengesellschaft, Berlin (DE)

( * ) Notice: Subject to any disclaimer, the term of this patent is extended or adjusted under 35 U.S.C. 154(b) by 0 days.

(21) Appl. No.: 10/069,284

(22) PCT Filed: Aug. 23, 2000

(86) PCT No.: PCT/EP00/08240

§ 371 (c)(1),
(2), (4) Date: Sep. 6, 2002

(87) PCT Pub. No.: WO01/14347

PCT Pub. Date: Mar. 1, 2001

(30) Foreign Application Priority Data

Aug. 25, 1999 (DE) ................................ 199 41 115

(51) Int. Cl.
*C07D 265/36* (2006.01)
*C07D 498/04* (2006.01)
*A61K 31/538* (2006.01)
*A61K 31/5383* (2006.01)

(52) U.S. Cl. ................ 514/229.8; 514/230.5; 514/224.5; 514/226.5; 544/105; 544/101; 544/52; 544/31

(58) Field of Classification Search ................ 544/105, 544/101; 514/229.8, 230.5
See application file for complete search history.

(56) References Cited

FOREIGN PATENT DOCUMENTS

| WO | WO 98/50372 | 11/1998 |
| WO | WO 99/12915 | 3/1999 |
| WO | WO 99/23092 | 5/1999 |

OTHER PUBLICATIONS

Organic Chemistry Text Book by Seyhan Ege (1989) p. 450-451.*
CASREACT search result printout performed on Jul. 14, 2004.*

* cited by examiner

*Primary Examiner*—Kahsay Habte
(74) *Attorney, Agent, or Firm*—Jacqueline S. Larson

(57) ABSTRACT

The invention relates to compounds of formula (I), the tautomeric and isomeric forms and salts thereof, in addition to a method for production and use thereof in medicaments.

(I)

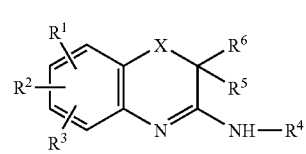

16 Claims, No Drawings

BENZOXAZINE AND BENZOTHIAZINE DERIVATIVES AND THE USE THEREOF IN MEDICAMENTS

The invention relates to benzoxazine and benzothiazine derivatives, the process for their production and their use in pharmaceutical agents.

In human cells, there exist at least three forms of nitrogen monoxide synthases, which convert arginine into nitrogen monoxide (NO) and citrulline. Two constitutive NO-synthases (NOS) were identified that are present as calcium/calmodulin-dependent enzymes in the brain (ncNOS or NOS 1) or in the endothelium (ecNOS or NOS 3). Another isoform is the inducible NOS (iNOS or NOS 2), which is a virtually $Ca^{++}$-independent enzyme and is induced after activation of different cells by endotoxin or other substances.

NOS-inhibitors and especially selective inhibitors of NOS 1, NOS 2 or NOS 3 are therefore suitable for treatment of different diseases, which are induced or aggravated by pathological concentrations of NO in cells. A number of reviews provide information on the action and inhibitors of NO-synthases. Mentioned are, for example: Drugs 1998, 1, 321 or Current Pharmac. Design 1997, 3, 447.

As NOS-inhibitors, different compounds are known. For example, arginine derivatives, aminopyridines, cyclic amidine derivatives, phenylimidazoles, etc., are described. It is known from WO 98/50372 that 3-amino-2H-1,4-benzoxazines or 3-amino-2H-1,4-benzothiazines inhibit nitrogen monoxide synthases in a potent and selective manner.

It has now been found that the heterocyclic compounds that are substituted according to the invention, compared to known compounds, have advantages and can be better used as pharmaceutical agents.

The invention relates to the compounds of formula I, their tautomeric and isomeric forms and salts

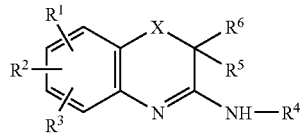

(I)

in which
X means O, $SO_m$
$R^1$ means —$(CHR^9)_n$—$NR^7$—A—$NR^8$—B, —$(CHR^9)_n$—$NR^7$—$(CH_2)_p$—C=R—$(CH_2)_q$—$NR^8$—D or —$(CHR^9)_n$—$NR^7$—B,
$R^2$ means hydrogen or
$R^1$ and $R^2$ together with two adjacent carbon atoms form a 5-, 6-, 7- or 8-membered ring, which is monocyclic or bicyclic, saturated or unsaturated and in which 1 or 2 $CH_2$ groups can be replaced by oxygen or carbonyl, and which is substituted with $(CHR^9)_r$—$NR^7$—A—$NR^8$—B, —$(CHR^9)_r$—$NR^7$—$(CH_2)_p$—C=R—$(CH_2)_q$—$NR^8$—D or —$(CHR^9)_r$—$NR^7$—B and can be substituted with $C_{1-4}$ alkyl,
$R^3$ means hydrogen, halogen, $NO_2$, cyano, $CF_3$, —$OCF_3$, —S—$R^9$, —O—$R^9$, $C_{3-7}$ cycloalkyl, —$NR^9$—C(=$NR^{10}$)—$R^{11}$, —NH—CS—$NR^{12}R^{13}$, NH—CO—$NR^{12}R^{13}$, —$SO_2NR^{12}R^{13}$, —CO—$NR^{12}R^{13}$, —CO—$R^4$, $NR^{15}R^6$, $C_{6-10}$ aryl, which optionally is substituted with halogen, cyano, $C_{1-4}$ alkyl, —S—$R^9$, or —O—$R^9$, 5- or 6-membered heteroaryl with 1 to 4 oxygen, sulfur or nitrogen atoms,
$C_{1-6}$ alkyl, which optionally is substituted with halogen, —$OR^9$, —$SR^9$, —$NR^{12}R^{13}$, =$NR^{12}$, =$NOC_{1-6}$ alkyl, =N—NHaryl, phenyl, $C_{3-7}$ cycloalkyl or 5- or 6-membered heteroaryl,
$C_{2-6}$ alkenyl, which optionally is substituted with halogen, $CONH_2$, C≡N or phenyl,
$C_{2-6}$ alkinyl, which optionally is substituted with halogen, $CONH_2$, C≡N or phenyl,
$R^4$ means hydrogen or acyl,
$R^5$ and $R^6$, independently of one another, mean hydrogen, $C_{3-7}$ cycloalkyl, phenyl, $C_{1-6}$ alkyl, $C_{2-6}$ alkenyl or $C_{2-6}$ alkynyl radicals, which can be substituted in each case with halogen, OH, O—$C_{1-6}$ alkyl, SH, S—$C_{1-6}$ alkyl, $NR^{15}R^{16}$, 5- or 6-membered heteroaryl with 1–3 N, O or S atoms, phenyl or $C_{3-7}$ cycloalkyl,
$R^7$ means hydrogen, $C_{1-6}$ alkyl, which can be substituted with phenyl, $COOC_{1-6}$ alkyl or $COC_{1-6}$ alkyl,
$R^8$ means hydrogen,
A means straight-chain or branched $C_{1-6}$ alkylene, straight-chain or branched $C_{2-6}$ alkenylene or —$(CH_2)_p$—Q—$(CH_2)_q$—,
B means —C=R—$(CH_2)_p$—U, —C=R—$NR^{15}R^{16}$, —$SOR^{12}$, —$SOR^{12}$, —C=O—O-aryl or —C=O—O-benzyl,
D means hydrogen or —$(CH_2)_p$—U,
R means oxygen or sulfur,
Q means $C_{3-7}$ cycloalkyl, indanyl, 5-, 6- or 7-membered saturated heterocycloalkyl with 1–2 N, O or S atoms, $C_6$–$C_{10}$ aryl or 5- or 6-membered heteroaryl with 1–3 N, O or S atoms, which can be anellated with benzene,
U means hydrogen, $C_{1-6}$ alkyl optionally substituted with halogen, $C_{3-7}$ cycloalkyl, indanyl, $C_{7-10}$ bicycloalkyl, $C_{6-10}$ aryl or 5- or 6-membered heteroaryl with 1–3 N, O or S atoms, which can be anellated with benzene, whereby the aryl and heteroaryl radical can be substituted with halogen, $C_{1-4}$ alkyl, $C_{1-4}$ alkoxy, $CF_3$, $NO_2$, $NH_2$, $N(C_{1-4}$ alkyl)$_2$, cyano, $CONH_2$, —O—$CH_2$—O—, —O—$(CH_2)_2$—O—, $SO_2NH_2$, OH, phenoxy or $COOC_{1-4}$ alkyl, or
$R^8$ and B together with the nitrogen atom form a 5- to 7-membered saturated heterocyclic compound, which contains a carbonyl or thiocarbonyl group and optionally can contain another oxygen, nitrogen or sulfur atom and can be substituted with $C_{1-4}$ alkyl or a phenyl, benzyl or benzoyl radical that is optionally substituted with halogen, or
$R^7$ and A together with the nitrogen atom form a 5- to 7-membered saturated heterocyclic compound, which can contain another oxygen, nitrogen or sulfur atom or forms an unsaturated 5-membered heterocyclic compound, which can contain 1 to 3 N atoms,
m means 0, 1 or 2,
n and r mean 0, 1 to 6,
p and q mean 0 to 6,
$R^9$ and $R^{10}$ mean hydrogen or $C_{1-6}$ alkyl,
$R^{11}$ means $C_{1-6}$ alkyl, —$NH_2$, —NH—$CH_3$, —NH—CN, $C_{6-10}$ aryl optionally substituted with halogen, $C_{1-4}$ alkyl or $CF_3$, or 5- or 6-membered heteroaryl with 1 to 4 nitrogen, sulfur or oxygen atoms that is optionally substituted with halogen, $C_{1-4}$ alkyl or $CF_3$,
$R^{12}$ and $R^{13}$ mean hydrogen, $C_{1-6}$ alkyl, phenyl optionally substituted with halogen or $C_{1-4}$ alkyl, benzyl optionally substituted with halogen or $C_{1-4}$ alkyl, or $C_{3-7}$ cycloalkyl,
$R^{14}$ means hydrogen, hydroxy, $C_{1-6}$ alkoxy, phenyl, $C_{1-6}$ alkyl optionally substituted with $CO_2H$, $CO_2C_{1-6}$ alkyl, hydroxy, $C_{1-4}$ alkoxy, halogen, $NR^{15}R_1$, $CONR^{12}R^{13}$, or phenyl, or $C_{2-6}$ alkenyl optionally substituted with phenyl, cyano, $CONR^{12}R^{13}$ or $CO_2C_{1-4}$ alkyl, $R^{15}$ and $R^{16}$ mean hydrogen, $C_{1-6}$ alkyl, phenyl optionally substituted with halogen or $C_{1-4}$ alkyl, or benzyl optionally substituted with halogen or $C_{1-4}$ alkyl, $R^{15}$ and $R^{16}$ together with the nitrogen atom form a saturated 5-, 6-, or 7-membered ring, which can contain another nitrogen, oxygen or sulfur atom and can be substituted with $C_{1-4}$ alkyl, or a phenyl, benzyl or benzoyl radical optionally substituted with halogen.

The compounds of formula I can be present as tautomers, stereoisomers or geometric isomers. The invention also comprises all possible isomers, such as E- and Z-isomers, S- and R-enantiomers, diastereomers, racemates and mixtures thereof, including the tautomeric compounds of Formulas Ia and Ib

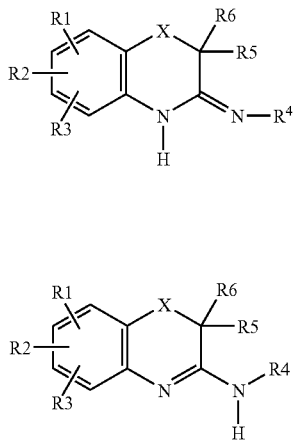

The physiologically compatible salts can be formed with inorganic and organic acids, such as, for example, oxalic acid, lactic acid, citric acid, fumaric acid, acetic acid, maleic acid, tartaric acid, phosphoric acid, HCl, HBr, sulfuric acid, p-toluenesulfonic acid, methanesulfonic acid, i.a.

For salt formation of acid groups, the inorganic or organic bases are also suitable, which are known for the formation of physiologically compatible salts, such as, for example, alkali hydroxides, such as sodium and potassium hydroxide, alkaline-earth hydroxides, such as calcium hydroxide, ammonia, amines such as ethanolamine, diethanolamine, triethanolamine, N-methylglucamine, tris-(hydroxymethyl)-methylamine, etc.

In each case, alkyl means a straight-chain or branched alkyl group, such as, e.g., methyl, ethyl, propyl, isopropyl, n-butyl, sec-butyl, tert-butyl, n-pentyl, sec-pentyl, tert-pentyl, neopentyl, n-hexyl, sec-hexyl, heptyl, or octyl.

If alkyl radical U is substituted with halogen, it can be halogenated in one or more places, in particular perhalogenated, such as $CF_3$, $C_2F_5$, $CH_2F$, 2-fluoroethyl.

Alkenyl and alkynyl substituents are in each case straight-chain or branched. For example, the following radicals can be mentioned: vinyl, 2-propenyl, 1-propenyl, 2-butenyl, 1-butenyl, 3-butenyl, 2-methyl-2-propenyl, ethinyl, 1-propinyl, 2-propinyl, 1-butinyl, 2-butinyl, 2-pentenyl, 4-hexenyl.

Cycloalkyl is defined respectively as cyclopropyl, cyclobutyl, cyclopentyl, cyclohexyl or cycloheptyl. As a bicyclic compound, for example, bicycloheptane and bicyclooctane can be mentioned.

Halogen means respectively fluorine, chlorine, bromine or iodine.

Aryl is defined respectively as naphthyl or phenyl, which can be substituted by the same or a different component in one to three places.

As heteroaryl radicals, which can be bonded via the heteroatom or a carbon atom, for example, the following 5- and 6-ring heteroaromatic compounds can be mentioned:

Imidazole, indole, isooxazole, isothiazole, furan, oxadiazole, oxazole, pyrazine, pyridazine, pyrimidine, pyridine, pyrazole, pyrrole, tetrazole, thiazole, triazole, thiophene, thiadiazole, benzimidazole, benzofuran, benzoxazole, isoquinoline, quinoline. As a heteroaryl radical, $2-C_{1-6}$ alkyl-3-amino-2H-1,4-benzoxazine and $2-C_{1-6}$-alkyl-3-keto-2H-1,4-benzoxazine are also suitable.

In the case of a substitution of the heteroaryl radical, the latter can be substituted by the same or a different component in one to three places.

As a preferred embodiment of $R^{11}$ in the meaning of heteroaryl, thienyl can be considered.

Saturated heterocyclic compounds are defined in each case as, for example, piperidine, pyrrolidine, morpholine, thiomorpholine, hexahydroazepine and piperazine. The heterocyclic compound can be substituted by the same or a different component in one to three places with $C_{1-4}$ alkyl or a phenyl, benzyl or benzoyl radical that is optionally substituted with halogen. For example, there can be mentioned: N-methyl-piperazine, 2,6-dimethylmorpholine, pyrrolidine, phenylpiperazine or 4-(4-fluorobenzoyl)-piperidine.

If $-NR^7A-$ together with the nitrogen atom forms an unsaturated heterocyclic compound, for example, imidazole, pyrrole, pyrazole and triazole can be mentioned.

Simple substitution is preferred for substituents $R^5$ and $R^6$ in 2-position of the oxazine or thiazine, whereby substituent $R^5$ in particular means $C_{1-6}$ alkyl and $R^6$ is hydrogen.

Substituent Q can be linked at any point via a C atom or optionally via an N atom.

If $R^1$ and $R^2$ together with two adjacent carbon atoms form a ring, the latter can be in 5,6- or 7,8- or especially 6,7-position of the benzoxazine or benzothiazine and has the formula

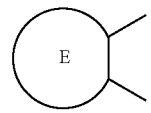

in which

E means a saturated or unsaturated $C_{3-8}$ alkylene radical, which is substituted in one to two places with $-(CHR^9)_r-NR^7-A-NR^8B$, $-(CHR^9)_r-NR^7-$ $(CH_2)_p-C=R-$ $(CH_2)_q-NR^8-D$ or $-(CHR^9)_r-NR^7-B$ and optionally is substituted in one to two places with $C_{1-4}$ alkyl and in which 1 or 2 $CH_2$ groups can be replaced by oxygen, carbonyl or its derivative, and whereby the alkylene radical can contain a slightly condensed benzene radical, such as, for example, indan, or can be present as a bicyclic compound, such as, for example, bicycloheptane.

Substituent r stands in particular for zero.

As structures of E, there can be mentioned, for example:

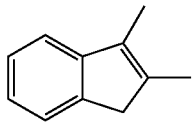

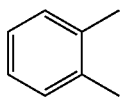

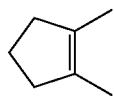

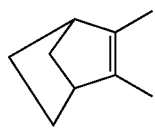

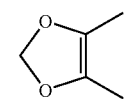

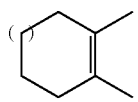

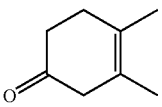

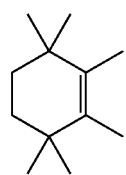

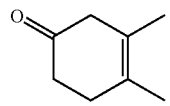

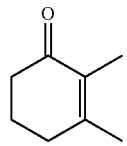

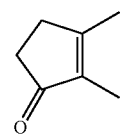

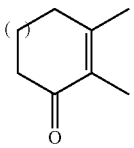

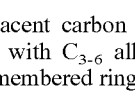

As carbonyl derivatives, for example, =NOH, =N—OC$_{1-6}$ alkyl, =NH—NH$_2$, and =N—NH-phenyl are suitable.

Preferably, two adjacent carbon atoms of the aromatic compound are linked with C$_{3-6}$ alkylene, especially C$_{3-4}$ alkylene, to a 5- to 8-membered ring E, especially to a 5- to 6-membered ring.

Acyl radical R$^4$ is derived from straight-chain or branched aliphatic C$_{1-6}$ carboxylic acids, such as, for example, formic acid, acetic acid, propionic acid, butyric acid, trimethylacetic acid or caproic acid or from known benzenesulfonic acids, which can be substituted with halogen or C$_{1-4}$ alkyl, and C$_{1-4}$ alkanesulfonic acids, such as, for example, methanesulfonic acid, and p-toluenesulfonic acid.

Substituent n preferably stands for 1–6, especially for 1.

Preferred embodiments of X are S and especially O.

Preferred embodiments of R$^3$, R$^4$, R$^7$ and R$^9$ are in each case hydrogen.

Substituent R$^1$ is preferably in 6-position.

Ring E is preferably substituted in one place, whereby the substituent is in 6-position.

A preferred embodiment of A is straight-chain or branched C$_{1-6}$ alkylene.

If R$^8$ and B together with the nitrogen atom form a saturated heterocyclic compound, in particular pyrrolidine-2-thione is meant.

Preferred embodiments of B are —C=R—(CH$_2$)$_p$—U, —C=R—NR$^{15}$R$^{16}$ and —SO$_2$R$^{12}$, in which R$^{12}$, especially C$_{1-6}$ alkyl, R$^{15}$ and R$^{16}$ mean in particular hydrogen, C$_{1-6}$ alkyl or phenyl, and —(CH$_2$)$_p$—U in particular means hydrogen, C$_{1-6}$ alkyl optionally substituted with halogen, or phenyl optionally substituted with halogen, C$_{1-4}$ alkyl, C$_{1-4}$ alkoxy or CF$_3$.

Preferred embodiments of D are hydrogen and —(CH$_2$)$_p$—U in the meaning of a benzyl radical that is optionally substituted with halogen, C$_{1-4}$ alkoxy, CF$_3$ or C$_{1-4}$ alkyl.

p and q preferably do not mean 0 simultaneously but rather either p or q means an alkylene radical with 1–6 carbon atoms.

The invention also relates to the use of the compounds according to the invention for the production of a pharmaceutical agent for treating diseases that are induced by the action of nitrogen monoxide at pathological concentrations. These include neurodegenerative diseases, inflammatory diseases, auto-immune diseases, and cardiovascular diseases.

For example, there can be mentioned:

Cerebral ischemia, hypoxia and other neurodegenerative diseases, which are brought into contact with inflammations, such as multiple sclerosis, amyotrophic lateral sclerosis and comparable sclerotic diseases, Parkinson's Disease, Huntington's Disease, Korksakoff's Disease, epilepsy, vomiting, sleep disorders, schizophrenia, depression, stress, pain, migraine, hypoglycemia, dementia, such as, e.g., Alzheimer's Disease, HIV-dementia and presenile dementia.

They are also suitable for treating diseases of the cardiovascular system and for treating auto-immune and/or inflammatory diseases, such as hypotension, ARDS (adult respiratory distress syndrome), sepsis or septic shock, rheumatoid arthritis, osteoarthritis, insulin-dependent diabetes mellitus (IDDM), inflammatory disease of the pelvis/intestine (bowel disease), meningitis, glomerulonephritis, acute and chronic liver diseases, diseases by rejection (for example allogenic heart, kidney or liver transplants) or inflammatory skin diseases such as psoriasis, etc.

Based on their profile of action, the compounds according to the invention are very well suited for inhibiting the neuronal NOS.

To use the compounds according to the invention as pharmaceutical agents, the latter are brought into the form of a pharmaceutical preparation, which in addition to the active ingredient contains vehicles, adjuvants and/or additives that are suitable for enteral or parenteral administration. The administration can be done orally or sublingually as a solid in the form of capsules or tablets or as a liquid in the form of solutions, suspensions, elixirs, aerosols or emulsions or rectally in the form of suppositories or in the form of injection solutions that can optionally also be administered subcutaneously, intramuscularly or intravenously, or topically or intrathecally. As adjuvants for the desired pharmaceutical agent formulation, the inert organic and inorganic support media that are known to one skilled in the art are suitable, such as, e.g., water, gelatin, gum arabic, lactose, starch, magnesium stearate, talc, plant oils, polyalkylene glycols, etc. Moreover, preservatives, stabilizers, wetting agents, emulsifiers or salts for changing the osmotic pressure or buffers can optionally be contained.

For parenteral administration, especially injection solutions or suspensions, especially aqueous solutions of the active compounds in polyhydroxyethoxylated castor oil, are suitable.

As vehicle systems, surface-active adjuvants such as salts of bile acids or animal or plant phospholipids, but also mixtures thereof as well as liposomes or their components can also be used.

For oral administration, especially tablets, coated tablets or capsules with talc and/or hydrocarbon vehicles or binders, such as, for example, lactose, corn or potato starch, are suitable. The administration can also be done in liquid form, such as, for example, as a juice, to which optionally a sweetener is added.

The dosage of the active ingredient can vary depending on method of administration, age and weight of the patient, type and severity of the disease that is to be treated and similar factors. The daily dose is 1–2000 mg, preferably 20–500 mg, whereby the dose can be given as an individual dose to be administered one time or divided into two or more daily doses.

The NOS-inhibitory action of the compounds of formula I and their physiologically compatible salts can be determined according to the methods by Bredt and Snyder in Proc. Natl. Acad. Sci. USA (1989) 86, 9030–9033.

The production of the compounds according to the invention is carried out in that a compound of formula II or its salt

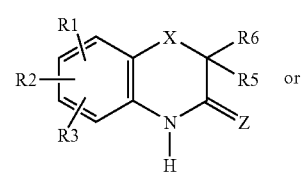

IIa or

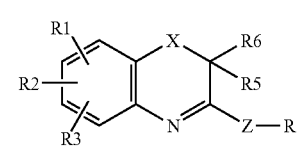

IIb in which

R$^1$, R$^2$, R$^1$, R$^1$, R$^6$ and X have the above-mentioned meaning, z is oxygen or sulfur and R means C$_{1-6}$ alkyl, is reacted with ammonia or primary amines, whereby existing amino groups are optionally intermediately protected and optionally then acylated, the isomers are separated or the salts are formed.

The reaction with ammonia is possible under pressure in autoclaves with excess ammonia at low temperatures (−78° C.) or by stirring in methanol that is saturated with ammonia at room temperature. Thiolactams are preferably reacted. If the reaction is with amines, first the iminoethers or iminothioethers are produced from lactam or thiolactam as intermediate compounds (e.g., with methyl iodide or methyl sulfate), and the latter are reacted with or without isolation of the intermediate compounds with the corresponding amines or their salts.

As amino protective groups, for example, carbamates, such as tert-butoxycarbonyl, benzyloxycarbonyl or acetyl, are suitable.

In the precursor stages, optionally sulfides are oxidized, esters are saponified, acids are esterified, hydroxy groups are etherified or acylated, amines are acylated, alkylated, diazotized, halogenated, NO$_2$ is introduced or reduced, reacted with isocyanates or isothiocyanates, the isomers are separated or the salts are formed.

The saponification of an ester group can be done basically or acidically by hydrolysis being performed at room temperature or at an elevated temperature up to boiling temperature of the reaction mixture in the presence of alkali hydroxides in ethanol or other alcohols or with use of acids, such as, e.g., hydrochloric acid, and optionally salts of aminobenzoxazines or -thiazines being further processed.

The esterification of carboxylic acid is done in a way that is known in the art with diazomethane or the corresponding alcohol in acid or in the presence of an activated acid derivative. As activated acid derivatives, for example, acid chloride, acid imidazolide or acid anhydride are suitable.

The reduction of an ester group to alcohol is carried out in a way that is known in the art with DIBAH in suitable solvents at low temperatures. The reductive amination of a ketone or a benzaldehyde with amine while adding boron hydride provides benzylic amines. With suitably selected diamines, symmetrical or unsymmetrical amino compounds are obtained after identical or different aldehydes are added.

In addition, a nitro group or halogen, especially bromine, can be introduced by electrophilic, aromatic substitution. Mixtures that are produced in this case can be separated in the usual way, also using HPLC. If a nitrile is present, the latter can be saponified according to known processes or can be converted into the corresponding amine, tetrazole or amidoxime, or it is in a substituted amidine by attacking substituted anilines or amines.

The Friedel-Crafts acylation is used successfully in lactams of type IIa, and then the lactam can be converted selectively into the thiolactam, or the acylation product can be reductively aminated.

The reduction of the nitro group or optionally the cyano group to the amino group is carried out catalytically in polar solvents at room temperature or at an elevated temperature under hydrogen pressure. As catalysts, metals such as Raney nickel or noble metal catalysts such as palladium or platinum optionally in the presence of barium sulfate or on vehicles are suitable. Instead of hydrogen, ammonium formate or formic acid can also be used in a known way. Reducing agents such as tin(II) chloride can also be used, such as complex metal hydrides optionally in the presence of heavy metal salts. The ester group can be advantageously introduced before the reduction as in Formula V. For nitro groups, reduction with zinc or iron in acetic acid has proven its value.

If a single or multiple alkylation of an amino group or a CH-acid carbon position is desired, alkylation can be performed with, for example, alkyl halides according to commonly used methods. Protection of the lactam group as an anion by a second equivalent base or by a suitable protective group optionally is necessary.

The acylation of the amino group is carried out in the usual way with, for example, an acid halide or acid anhydride, optionally in the presence of a base.

The introduction of the halogens chlorine, bromine or iodine via the amino group can also be carried out, for example, according to Sandmeyer, by the diazonium salts that are formed intermediately with nitrites being reacted with Cu(I) chloride or Cu(I) bromide in the presence of the corresponding acids such as hydrochloric acid or hydrobromic acid or being reacted with potassium iodide.

Benzyl alcohols can be converted into corresponding benzyl halides as usual with methanesulfonyl chloride.

The introduction of an $NO_2$ group is possible by a number of known nitration methods. For example, nitration can be performed with nitrates or with nitronium tetrafluoroborate in inert solvents, such as halogenated hydrocarbons or in sulfolane or glacial acetic acid. Introduction by, e.g., nitrating acid in water or concentrated sulfuric acid as a solvent is also possible at temperatures of between −10° C. and 30° C.

The isomer mixtures can be separated into enantiomers or E/Z-isomers according to commonly used methods, such as, for example, crystallization, chromatography or salt formation. The enantiomers or enantiomer-pure diastereomers can also be obtained by chromatography on chiral phases as well as by stereoselective syntheses.

The production of the salts is carried out in the usual way, by a solution of the compound of Formula I—optionally also with protected amino groups—being mixed with the equivalent amount of acid or excess acid, which optionally is in solution, and the precipitate being separated or the solution being worked up in the usual way.

Nucleophilic substitution of benzyl halides with secondary amines yields the corresponding benzylamines.

Thiolactams of formula IIa (Z=S) are obtained from, for example, lactams with phosphorus pentasulfide ($P_4S_{10}$) or Lawesson's reagent (2,4-bis(4-methoxyphenyl)-1,3,2,4-dithiaphosphetane-2,4-disulfide) in suitable solvents, and compounds of Formula IIb can be obtained by, for example, reaction with Meerwein reagent (trimethyloxonium tetrafluoroborate).

If the production of the starting compounds is not described, the latter are known and commercially available or can be produced analogously to known compounds or according to processes that are described here.

The production of the compounds of Formula IIa can be carried out, for example, in that a compound of Formula III

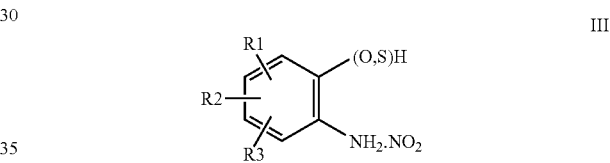

in which $R^1$ to $R^3$ have the above-mentioned meaning, is reacted with a compound of Formula IV

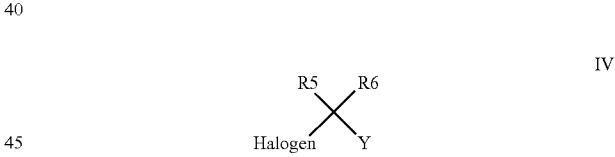

in which $R^5$ and $R^6$ have the above-mentioned meaning, and Y is a reactive carboxyl group such as acid halide, nitrile, carboxylic acid ester, and optionally is reductively cyclized, or in that a compound of Formula V

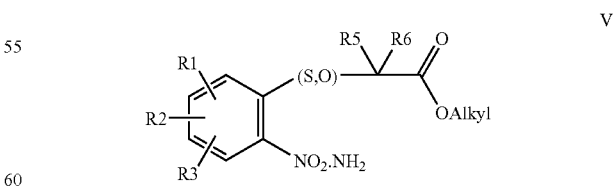

is reductively cyclized.

Aromatic thiols of type III are obtained, i.a., as described in Chem. Pharm. Bull. 1991, 39, 2888 and the literature that is mentioned there by rearrangement of the corresponding dimethylaminothiocarbamates.

The introduction of substituents $R^1$ to $R^3$ can be carried out in the stage of the compounds of Formula III or II.

For the production of compounds of Formula II, the aldehyde or the ketone of the corresponding 1,4-benzoxazine-3-one or 1,4-benzothiazine-3(4H)-one can be reductively aminated. This can also be done in two places with suitably selected diamines. Diamines can also be reacted with the aldehyde of 1,4-benzoxazin-3-one and simultaneously with other suitably selected aldehydes. If the introduction of a heteroaryl radical Q is desired, the corresponding halogen derivative can be substituted nucleophilically with amine. If a primary or secondary amino group is present, it may be advantageous to protect the latter intermediately, for example by introduction of a tert-butoxycarbonyl group, which is cleaved in the usual way after the amidine formation.

Monoacylated diamines are also obtained, as described in the literature (Synthesis 11; 1988; 917–918), by reaction of benzamides with diamine with release of ammonia.

New compounds were identified by one or more of the following methods: melting point, mass spectroscopy, NMR. NMR spectra were measured with a Bruker 300 MHz device; the (deuterated) solvents are abbreviated as follows: $CDCl_3$ (chloroform), DMSO (dimethyl sulfoxide). Alterations are indicated in delta and ppm. Here: m means multiplet, several signals; s means singlet; d means doublet; dd means double doublet, etc.; tr means triplet; q means quartet; H means hydrogen protons; J means coupling constant. In addition, THF means tetrahydrofuran, DMF means N,N-dimethylformamide, MeOH means methanol, EE means ethyl acetate, ml means milliliter, and RT means room temperature. All solvents are p.A. grade, unless otherwise indicated. All reactions are performed under protective gas, unless these are aqueous solutions.

Below, the production of several precursors, intermediate products and products is described by way of example.

Starting Compounds

A

Mono-N-trifluoroacetyl-1,4-butanediamine

Trifluoroacetamide and 1,4-butanediamine are reacted as described in the literature (Synthesis 11: 1988; 917–918).

The following, i.a., are produced in the same way:
Mono-N-β-chlorobenzoyl-1,4-butanediamine
mono-N-benzoyl-1,4-butanediamine
mono-N-trifluoroacetyl-1,5-pentanediamine
mono-N-β-chlorobenzoyl-1,5-pentanediamine
mono-N-methanesulfonyl-1,5-pentanediamine The synthesis of 6-formyl-2-methyl-2H-1,4-benzoxazin-3(4H)-one is described in DE-198 26 232.9, as well as that of 6-formyl-2-ethyl-2H-1,4-benzoxazin-3(4H)-one and 6-formyl-2-propyl-2H-1,4-benzoxazin-3(4H)-one.

6-{[N-(4-Chlorobenzyl)-pentanecarboxylic acid amide-6-yl]-aminomethyl}-2-methyl-2H-1,4-benzoxazin-3(4H)-one In 4 ml of methanol, 100 mg of epsilon-amino-pentanecarboxylic acid-para-chlorobenzylamide hydrochloride (ε-aminocaproyl-para-chlorobenzylamide hydrochloride, commercially available product) is mixed with 0.07 ml of triethylamine. 61 mg of 6-formyl-2-methyl-2H-1,4-benzoxazin-3(4H)-one is added to it. It is stirred for 60 minutes at room temperature, and then 16 mg of potassium borohydride is added. After 2 hours at room temperature, it is poured into water, extracted three times with ethyl acetate, and the organic phase is washed with brine. It is dried with magnesium sulfate, and 1.29 mg of crude product is concentrated by evaporation.

In the same way, the following are produced from monoacylated diamines:
6-{[N-(Trifluoroacetyl)-aminobut-4-yl]-aminomethyl}-2-methyl-2H-1,4-benzoxazin-3(4H)-one
6-{[N-(4-chlorobenzoyl)-aminobut-4-yl]-aminomethyl}-2-methyl-2H-1,4-benzoxazin-3(4H)-one
6-{[N-benzoyl-aminobut-4-yl]-aminomethyl}-2-methyl-2H-1,4-benzoxazin-3(4H)-one
6-{[N-(trifluoroacetyl)-aminopent-5-yl]-aminomethyl}-2-methyl-2H-1,4-benzoxazin-3(4H)-one
6-{[N-(4-chlorobenzoyl)-aminopent-5-yl]-aminomethyl}-2-methyl-2H-1,4-benzoxazin-3(4H)-one From 3-(N-pyrrolidin-2-one)-propylamine:
6-{[N-(Pyrrolidin-2-one)-prop-3-yl]-aminomethyl}-2-methyl-2H-1,4-benzoxazin-3(4H)-one From 6-keto-6,7,8,9-tetrahydro-2-methyl-2H-naphth[2,3-b]-1,4-oxazin-3(4H)-one
6-{[N-(Trifluoroacetyl)-aminobut-4-yl]-amino}-6,7,8,9-tetrahydro-2-methyl-2H-naphth[2,3-b]-1,4-oxazin-3(4H)-one
6-{[N-methanesulfonylamino-pent-5-yl]-aminomethyl}-2-methyl-2H-1,4-benzoxazin-3(4H)-one

B

N-{[2-Methyl-2H-1,4-benzoxazin-3(4H)-one]-6-yl}-methyl-amino-n-butyl-N'-phenylurea 0.07 ml of triethylamine is added to 80 mg of 6-(omega-amino-n-butyl-aminomethyl)-2-methyl-2H-1,4-benzoxazin-3(4H)-one dihydrochloride in 3 ml of THF and 2 ml of DMF, then 27 microliters of phenylisocyanate is added, and it is stirred for 24 hours at room temperature. It is poured into a little water, extracted with ethyl acetate, and the organic phase is dried with magnesium sulfate and concentrated by evaporation. Crude product 95 mg.

The product also contains N-{[2-methyl-2H-1,4-benzoxazin-3(4H)-on]-6-yl}-methyl-(Phenylaminocarbonyl)-amino-n-butyl-N'-phenylurea.

C

6-{[N-(4-Chlorobenzyl)-Pentanecarboxylic acid amide-6-yl]-(tert-butyloxycarbonyl)-aminomethyl}-2-methyl-2H-1,4-benzoxazin-3(4H)-one 129 mg of 6-{[N-(4-chlorobenzyl)-pentanecarboxylic acid amide-6-yl]-aminomethyl}-2-methyl-2H-1,4-benzoxazin-3(4H)-one in 8 ml of dichloromethane is stirred while 0.127 ml of triethylamine and 163 mg of di-tert-butyl dicarbonate are being added. After 12 hours at room temperature, it is diluted with dichloromethane, washed with sodium bicarbonate and then with brine. The organic phase is dried and concentrated by evaporation. After column chromatography with hexane and ethyl acetate, 98 mg of product results.

In the same way, the following are produced:
6-{[N-(Trifluoroacetyl)-aminobut-4-yl]-(tert.-butyloxycarbonyl)-aminomethyl}-2-methyl-2H-1,4-benzoxazin-3(4H)-one
6-{[N-(4-chlorobenzoyl)-aminobut-4-yl]-(tert.-butyloxycarbonyl)-aminomethyl}-2-methyl-2H-1,4-benzoxazin-3(4H)-one
6-{[N-benzoyl-aminobut-4-yl]-(tert.-butyloxycarbonyl)-aminomethyl}-2-methyl-2H-1,4-benzoxazin-3(4H)-one
6-{[N-(Trifluoroacetyl)-aminopent-5-yl]-(tert.-butyloxycarbonyl)-aminomethyl}-2-methyl-2H-1,4-benzoxazin-3(4H)-one
6-{[N-(4-chlorobenzoyl)-aminopent-5-yl]-(tert.-butyloxycarbonyl)-aminomethyl}-2-methyl-2H-1,4-benzoxazin-3(4H)-one N-{[2-Methyl-2H-1,4-benzoxazin-3(4H)-one]-6-yl)-methyl-(tert.-butyloxycarbonyl)-amino-n-butyl-N'-phenylurea 6-{[N-(pyrrolidin-2-one)-prop-3-yl]-(tert.-butyloxycarbonyl)-aminomethyl}-2-methyl-2H-1,4-benzoxazin-3 (4H)-one 6-{[N-(trifluoroacetyl)-aminobut-4-yl]-(tert.-butyloxycarbonyl)-amino}-6,7,8,9-tetrahydro-2-methyl-2H-naphth[2,3-b]-1,4-oxazin-3(4H)-one 6-{[N-methanesulfonylamino-pent-5-yl]-(tert.-butyloxycarbonyl)-aminomethyl)-2-methyl-2H-1,4-benzoxazin-3(4H)-one

D

6-{[N-(4-Chlorobenzyl)-pentanecarboxylic acid-amide-6-yl]-(tert.-butyloxycarbonyl)-aminomethyl}-2-methyl-2H-1,4-benzoxazine-3(4H)-thione 72 mg of Lawesson's reagent is added at room temperature to 95 mg of 6-{[N-(4-chlorobenzyl)-pentanecarboxylic acid amide-6-yl]-(tert.-butyloxycarbonyl)-aminomethyl}-2-methyl-2H-1,4-benzoxazin-3(4H)-one in 3 ml of dimethoxyethane, and it is stirred for 8 more hours. After concentration by evaporation and column chromatography with hexane/ethyl acetate 2:1, 38 mg of product and 53 mg of 6-{[N-(4-chlorobenzyl)-pentanecarboxylic acid thioamide-6-yl]-(tert.-butyloxycarbonyl)-aminomethyl}-2-methyl-2H-1,4-benzoxazine-3(4H)-thione result.

In the same way, the following are produced:

6-{[N-(Trifluorothioacetyl)-aminobut-4-yl]-(tert.-butyloxycarbonyl)-aminomethyl}-2-methyl-2H-1,4-benzoxazine-3(4H)-thione and 6-{[N-(trifluoroacetyl)-aminobut-4-yl]-(tert.-butyloxycarbonyl)-aminomethyl}-2-methyl-2H-1,4-benzoxazine-3(4H)-thione 6-{[N-(4-Chlorobenzoyl)-aminobut-4-yl]-(tert.-butyloxycarbonyl)-aminomethyl}-2-methyl-2H-1,4-benzoxazine-3(4H)-thione and 6-{[N-(4-chlorothiobenzoyl)-aminobut-4-yl]-(tert.-butyloxycarbonyl)-aminomethyl}-2-methyl-2H-1,4-benzoxazine-3(4H)-thione 6-{[N-Thiobenzoyl-aminobut-4-yl]-(tert.-butyloxycarbonyl)-aminomethyl}-2-methyl-2H-1,4-benzoxazine-3(4H)-thione 6-{[N-(Trifluorothioacetyl)-aminopent-5-yl]-(tert.-butyloxycarbonyl-aminomethyl}-2-methyl-2H-1,4-benzoxazine-3(4H)-thione 6-{[N-(thio-4-chlorobenzoyl)-aminopent-5-yl]-(tert.-butyloxycarbonyl)-aminomethyl}-2-methyl-2H-1,4-benzoxazine-3(4H)-thione N-{[2-Methyl-2H-1,4-benzoxazine-3(4H)-thione]-6-yl)-methyl-(tert.-butyloxycarbonyl)-amino-n-butyl-N'-phenylurea 6-{[N-(Pyrrolidine-2-thione)-prop-3-yl]-(tert.-butyloxycarbonyl)-aminomethyl}-2-methyl-2H-1,4-benzoxazine-3(4H)-thione 6-{[N-(Trifluorothioacetyl)-aminobut-4-yl]-(tert.butyloxycarbonyl)-amino}-6,7,8,9-tetrahydro-2-methyl-2H-naphth[2,3-b]-1,4-oxazine-3(4H)-thione and 6-{[N-(trifluoroacetyl)-aminobut-4-yl]-(tert.-butyloxycarbonyl)-amino}-6.7,8,9-tetrahydro-2-methyl-2H-naphth-2,3-b]-1,4-oxazine-3(4H)-thione 6-{[N-Methanesulfonylamino-pent-5-yl]-(tert.-butyloxycarbonyl)-aminomethyl}-2-methyl-2H-1,4-benzoxazin-3(4H)-thione

EXAMPLE 1

6-{[N-(4-Chlorobenzyl)-pentanecarboxylic acid thioamide-6-yl]-(tert.-butyloxycarbonyl)-aminomethyl}-3-amino-2-methyl-2H-1,4-benzoxazine 50 mg of 6-([N-(4-chlorobenzyl)-pentanecarboxylic acid thioamide-6-yl]-(tert.-butyloxycarbonyl)-aminomethyl)-2-methyl-2H-1,4-benzoxazine-3(4H)-thione in 50 ml of saturated ammonia solution is stirred in methanol (commercially available). After one day at room temperature, the crude product is obtained after concentration by evaporation. Column chromatography with ethyl acetate purifies the product. A 92% yield results.

MS (ei): 544 (7%), 545 (3%), 546 (4%) m/z.

In the same way, the following are produced:

6-{[N-(Trifluoroacetyl)-aminobut-4-yl]-(tert.-butyloxycarbonyl)-aminomethyl}-3-amino-2-methyl-2H-1,4-benzoxazine 6-{[N-trifluorothioacetyl)-aminobut-4-yl]-(tert.-butyloxycarbonyl)-aminomethyl}-3-amino-2-methyl-2H-1,4-benzoxazine 6-{[N-(4-Chlorobenzoyl)-aminobut-4-yl]-(tert.-butyloxycarbonyl)-aminomethyl}-3-amino-2-methyl-2H-1,4-benzoxazine 6-{[N-(4-chlorothiobenzoyl)-aminobut-4-yl]-(tert.-butyloxycarbonyl)-aminomethyl}-3-amino-2-methyl-2H-1,4-benzoxazine 6-{[N-benzoyl-aminobut-4-yl]1-(tert.-butyloxycarbonyl)-aminomethyl}-3-amino-2-methyl-2H-1,4-benzoxazine 6-{[N-(trifluoroacetyl)-aminopent-5-yl]-(tert.-butyloxycarbonyl)-aminomethyl}-3-amino-2-methyl-2H-1,4-benzoxazine 6-{[N-(4-chlorobenzoyl)-aminopent-5-yl]-(tert.-butyloxycarbonyl)-aminomethyl}-3-amino-2-methyl-2H-1,4-benzoxazine N-[(3-amino-2-methyl-2H-1,4-benzoxazine-6-yl)-methyl-(tert-butyloxycarbonyl)-amino]-n-butyl-N'-phenylurea 6-{[N-(pyrrolidine-2-thione)-prop-3-yl]-(tert.-butyloxycarbonyl)-aminomethyl}-3-amino-2-methyl-2H-1,4-benzoxazine MS (ei): 432 (27%), 433 (6%) m/z 6-{[N-(Trifluoroacetyl)-aminobut-4-yl]-(tert.-butyloxycarbonyl)-amino}-6,7,8,9-tetrahydro-3-amino-2-methyl-2H-naphth[2,3-b]-1,4-oxazine 6-{[N-Methanesulfonylamino-pent-5-yl]-(tert.-butyloxycarbonyl)-aminomethyl}-3-amino-2-methyl-2H-1,4-benzoxazine MS (ei): 454 (6%), 455 (2%) m/z

EXAMPLE 2

6-{[N-(4-Chlorobenzyl)-pentanecarboxylic acid thioamide-6-yl]-aminomethyl}-3-amino-2-methyl-2H-1,4-benzoxazine dihydrochloride 45 mg of 6-{[N-(4-chlorobenzyl)-pentanecarboxylic acid thioamide-6-yl]-(tert.-butyloxycarbonyl)-aminomethyl}-3-amino-2-methyl-2H-1,4-benzoxazine is stirred in 1 ml of THF with 1 ml of 4N hydrochloric acid (solution in dioxane). After 12 hours, it is evaporated to the dry state. 32 mg of product (76% yield) is obtained.

[1H]-NMR (MeOH): 7.28 1H, 7.22 4H, 7.21 1H, 7.05 d 1H, 5.16 q 1H, 4.7 2H, 4.1 s broad 2H, 2.93 m 2H, 2.58 tr 2H, 1.7 m 4H, 1.48 d 3H, 1.33 m 2H.

In the same way, the following are produced:

6-{[N-(Trifluoroacetyl)-aminobut-4-yl]-aminomethyl}-3-amino-2-methyl-2H-1,4-benzoxazine dihydrochloride
[1H]-NMR (DMSO): 9.5 s broad 1H and 9.2 s broad 1H, 7.42 d 1H J=1Hz, 7.33 dd 1H, 7.11 d J=8 Hz 1H, 5.32 q 1H, 4.09 s broad 2H, 3.2 m 2H, 2.9 m 2H, 1.65 m 2H and 1.55 m 2H, 1.49 d 3H.

6-{[N-(Trifluorothioacetyl)-aminobut-4-yl]-aminomethyl}-3-amino-2-methyl-2H-1,4-benzoxazine dihydrochloride 6-{[N-(4-chlorobenzoyl)-aminobut-4-yl]-aminomethyl}-3-amino-2-methyl-2H-1,4-benzoxazine dihydrochloride
[1H]-NMR (DMSO): 9.5 s broad 1H, 9.3 s broad 1H and 8.6 s broad 1H, 7.9 d 2H, 7.53 d 2H, 7.45 d 1H, J=1Hz, 7.32 dd 1H, 7.11 d 1H, 5.35 q 1H, 4.1 s broad 2H, 3.3 m 2H, 2.9 m 2H, 1.7 m 2H and 1.6 m 2H, 1.49 d 3H. MS (ei): 400, 401 m/z (visible as a free base).

6-{[N-(4-Chlorothiobenzoyl)-aminobut-4-yl]-aminomethyl}-3-amino-2-methyl-2H-1,4-benzoxazine dihydrochloride 6-{[N-benzoyl-aminobut-4-yl]-aminomethyl}-3-amino-2-methyl-2H-1,4-benzoxazine dihydrochloride 6-{[N-(trifluoroacetyl)-aminopent-5-yl]-aminomethyl}-3-amino-2-methyl-2H-1,4-benzoxazine dihydrochloride 6-{[N-(4-chlorobenzoyl)-aminopent-5-yl]-aminomethyl}-3-amino-2-methyl-2H-1,4-benzoxazine dihydrochloride N-{[3-amino-2-methyl-2H-1,4-benzoxazine-6-yl]-methylamino)-n-butyl-N'-phenylurea dihydrochloride 6-{[N-(pyrrolidine-2-thione)-prop-3-yl]-aminomethyl}-3-amino-2-methyl-2H-1, 4-benzoxazine dihydrochloride
[1H]-NMR (DMSO): 9.7 broad 1H, 9.5 broad 1H and 9.3 broad 1H, 7.45 d 1H, 7.33 dd 1H, 7.13 d 1H, 5.35 q 1H, 4.11 s broad 2H, 3.7 m 4H, 3.4 m 2H, 2.9 m 2H, 2.0 m 4H, 1.51 d 3H.

6-{[N-(Trifluoroacetyl)-aminobut-4-yl]-amino}-6,7,8,9-tetrahydro-3-amino-2-methyl-2H-naphth[2,3-b]-1,4-oxazine dihydrochloride
[1H]-NMR(MeOH); 7.29 s 1H, 6.85 s 1H, 5.13 q 1H, 4.4 m 1H in 6-position, 3.22 m 2H, 3.08 tr 2H, 2.8 m 2H, 2.7 m 2H, 2.15 m 1H, 2.0 m 1H, 1.75 m 2H, 1.6 m 2H, 1.45 m 2H, 1.47 d 3H, MS (ei): 397 (11%), 398 (4%) m/z (fragment of free base).

6-{[N-Methanesulfonylamino-pent-5-yl]-aminomethyl}-3-amino-2-methyl-2H-1,4-benzoxazine dihydrochloride
[1H]-NMR(MeOH): 7.31 d 1H J=1Hz, 7.23 dd 1H, 7.05 d 1H, 5.18 q 1H, 4.10 s broad 2H, 3.5 m 2H, 2.99 m 4H, 2.82 s 3H methyl, 1.8 to 1.4 m 4H, 1.48 d 3H.
MS (ei): 353 (2%), 354 (2%) m/z (fragment of free base).

The invention claimed is:
1. A compound of the formula I, a tautomeric or isomeric form thereof or a salt thereof:

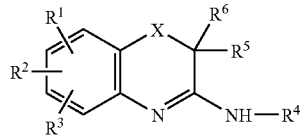

(I)

in which
X means O;
R¹ means —(CHR⁹)ₙ—NR⁷—A—NR⁸—B, —(CHR⁹)ₙ—NR⁷—(CH₂)ₚ—CR—(CH₂)_q—NR⁸—D, or —(CHR⁹)ₙ—NR⁷—B;
R² means hydrogen; or R¹ and R² together with two adjacent carbon atoms form a 5-, 6-, 7- or 8-membered ring, which is monocyclic or bicyclic, saturated or unsaturated and in which 1 or 2 CH₂ groups are optionally replaced by oxygen or carbonyl, and which is substituted with —(CHR⁹)ᵣ—NR⁷—A—NR⁸—B, —(CHR⁹)ᵣ—NR⁷—(CH₂)ₚ—CR—(CH₂)_q—NR⁸—D, or —(CHR⁹)ᵣ—NR⁷—B and is optionally substituted with C₁₋₄alkyl;

R³ means hydrogen, halogen, NO₂, cyano, CF₃, —OCF₃, —S—R⁹, —O—R⁹, C₃₋₇cycloalkyl, —NR⁹—C(=NR¹⁰)—R¹¹, —NH—CS—NR¹²R¹³, —NH—CO—NR¹²R¹³, —SO₂NR¹²R¹³, —CO—NR¹²R¹³, —CO—R¹⁴, —NR¹⁵R¹⁶, C₆₋₁₀aryl which optionally is substituted with halogen, cyano, C₁₋₄alkyl, —S—R⁹ or —O—R⁹; or 5- or 6-membered heteroaryl with 1 to 4 oxygen, sulfur or nitrogen atoms: or C₁₋₆alkyl, which optionally is substituted with halogen, —OR9, —SR⁹, —NR¹²R¹³, =NR¹², =NOC₁₋₅alkyl, =N—NH-aryl, phenyl, C₃₋₇cycloalkyl or 5- or 6-membered heteroaryl; or C₂₋₅alkenyl, which optionally is substituted with halogen, CONH₂, CN or phenyl; or C₂₋₆alkynyl, which optionally is substituted with halogen, CONH₂, CN or phenyl;

R⁴ means hydrogen or acyl;

R⁵ and R⁶, independently of one another, mean hydrogen, C₃₋₇cycloalkyl, phenyl, C₁₋₆alkyl, C₂₋₆alkenyl or C₂₋₆alkynyl radicals, which are optionally substituted in each case with halogen, OH, O—C₁₋₆alkyl, SH, S—C₁₋₆alkyl, NR¹⁵R¹⁶, 5- or 6-membered heteroaryl with 1–3 N, O or S atoms, phenyl or C₃₋₇cycloalkyl;

R⁷ means hydrogen or C₁₋₆alkyl, which is optionally substituted with phenyl, COOC₁₋₆alkyl or COC₁₋₆alkyl;

R⁸ means hydrogen;

A means straight-chain or branched C₁₋₄alkylene, straight-chain or branched C₂₋₆alkenylene or —(CH₂)ₚ—Q—(CH₂)_q—;

B means —CR—(CH₂)ₚ—U, —CR—NR¹⁵R¹⁶, —SOR¹², —SO₂R¹², —COO-aryl, or —COO-benzyl;

D means hydrogen or —(CH₂)ₚ—U;

R means oxygen or sulfur;

Q means C₃₋₇cycloalkylene, indanylene, 5-, 6- or 7-membered saturated heterocyclo-alkylene with 1–2 N, O or S atoms in the heterocyclo ring, C₆–C₁₀ arylene, or 5- or 6-membered heteroarylene with 1–3 N, O or S atoms which is optionally annellated with benzene;

U means hydrogen, C₁₋₆alkyl optionally substituted with halogen, C₃₋₇cycloalkyl, indanyl, C₇₋₁₀bicycloalkyl, C₆₋₁₀aryl or 5- or 6-membered heteroaryl with 1–3 N, O or S atoms which is optionally annellated with benzene, whereby the aryl and heteroaryl radical are optionally substituted with halogen, C₁₋₄alkyl, C₁₋₄alkoxy, CF₃, NO₂, NH₂, —N(C₁₋₄ alkyl)₂, cyano, —CONH₂, —O—CH₂—O—, —O—(CH₂)₂—O—, SO₂NH₂, OH, phenoxy or —COOC₁₋₄alkyl; or R⁸ and B together with the nitrogen atom to which they are bonded form a 5- to 7-membered saturated heterocyclic group, which contains an oxo or thioxo group on the ring and optionally contains another oxygen, nitrogen or sulfur atom and is optionally substituted with C₁₋₄alkyl or a phenyl, benzyl or benzoyl radical that is optionally substituted with halogen; or R[7] and A together with the nitrogen atom to which they are bonded form a 5- to 7-membered saturated heterocyclic group, or form an unsaturated 5-membered heterocyclic group;

m means 0, 1 or 2;

n and r independently of each other mean 0 to 6;

p and q independently of each other mean 0 to 6;

R[9] and R[10] independently of each other mean hydrogen or $C_{1-6}$alkyl;

R[11] means $C_{1-6}$alkyl, —$NH_2$, —NH—$CH_3$, —NH—CN, $C_{6-10}$aryl optionally substituted with halogen, $C_{1-4}$alkyl or $CF_3$, or 5- or 6-membered heteroaryl with 1 to 4 nitrogen, sulfur or oxygen atoms that is optionally substituted with halogen, $C_{1-4}$alkyl or $CF_3$;

R[12] and R[13] independently of each other mean hydrogen, $C_{1-4}$ alkyl, phenyl optionally substituted with halogen or $C_{1-4}$ alkyl, benzyl optionally substituted with halogen or $C_{1-4}$alkyl, or $C_{3-7}$cycloalkyl;

R[14] means hydrogen, hydroxy, $C_{1-6}$alkoxy, phenyl, $C_{1-4}$alkyl (optionally substituted with $CO_2H$, $CO_2C_{1-6}$ alkyl, hydroxy, $C_{1-4}$alkoxy, halogen, $NR^{15}R^{16}$, $CONR^{12}R^{13}$, or phenyl), or $C_{2-6}$ alkenyl (optionally substituted with phenyl, cyano, $CONR^{12}R^{13}$ or $CO_2C_{1-4}$ alkyl);

R[15] and R[16] independently of each other mean hydrogen, $C_{1-6}$alkyl, phenyl optionally substituted with halogen or $C_{1-4}$ alkyl, or benzyl optionally substituted with halogen or $C_{1-4}$alkyl; or R[15] and R[16] together with the nitrogen atom to which they are bonded form a saturated 5-, 6-, or 7-membered ring, which optionally contains a nitrogen, oxygen or sulfur atom and is optionally substituted with $C_{1-4}$alkyl, or a phenyl, benzyl or benzoyl radical optionally substituted with halogen.

2. A compound of claim 1, in which R[6] is hydrogen.

3. A compound of claim 1, in which R[5] is $C_{1-6}$alkyl.

4. A compound of claim 1, in which R[4] is hydrogen.

5. A compound of claim 1, in which R[3] is hydrogen.

6. A compound of claim 1, in which A is a straight-chain or branched $C_{1-6}$alkylene.

7. A compound of claim 1, which is:

6-{[N-(trifluoroacetyl)-aminobut-4-yl]-aminomethyl}-3-amino-2-methyl-2H-1,4-benzoxazine dihydrochloride;

6-{[N-trifluorothioacetyl)-aminobut-4-yl]aminomethyl}-3-amino-2-methyl-2H-1,4-benzoxazine dihydrochloride;

6-{[N-(4-chlorobenzoyl)-aminobut-4-yl]aminomethyl}-3-amino-2-methyl-2H-1,4-benzoxazine dihydrochloride;

6-{[N-(4-chlorothiobenzoyl)-aminobut-4-yl]-aminomethyl}-3-amino-2-methyl-2H-1,4-benzoxazine dihydrochloride;

6-{[N-benzoyl-aminobut-4-yl]aminomethyl}3-amino-2-methyl-2H-1,4-benzoxazine dihydrochloride;

6-{[N-(trifluoroacetyl-aminopent-5-yl]-aminomethyl}-3-amino-2-methyl-2H-1,4-benzoxazine dihydrochloride;

6-{[N-(4-chlorobenzoyl)-aminopent-5-yl]-aminomethyl}-3-amino-2-methyl-2H-1,4-benzoxazine dihydrochloride;

N-{[3-amino-2-methyl-2H-1,4-benzoxazine-6-yl]-methylamino}-n-butyl-N'-phenylurea dihydrochloride;

6-{[N-(pyrrolidine-2-thione)-prop-3-yl]-aminomethyl}-3-amino-2-methyl-2H-1,4-benzoxazine dihydrochloride;

6-{[N-(trifluoroacetyl)-aminobut-4-yl]-amino}-6,7,8,9-tetrahydro-3-amino-2-methyl-2H-naphth[2,3-b]-1,4-oxazine dihydrochloride; or 6{[N-methanesulfonylamino-pent-5-yl]-aminomethyl}amino-2-methyl-2H-1,4-benzoxazine dihydrochloride.

8. A pharmaceutical composition which comprises a compound according to claim 1 and one or more pharmaceutically common vehicles or adjuvants.

9. A compound of claim 1, wherein:

aryl is naphthyl or phenyl, each of which is optionally substituted in one to three places;

heteroaryl is imidazole, indole, isooxazole, isothiazole, furan, oxadiazole, oxazole, pyrazine, pyridazine, pyrimidine, pyridine, pyrazole, pyrrole, tetrazole, thiazole, triazole, thiophene, thiadiazole, benzimidazole, benzofuran, benzoxazole, isoquinoline, or quinoline, each of which is optionally substituted in one to three places;

saturated heterocyclic group is piperidine, pyrrolidine, morpholine, thiomorpholine, hexahydroazepine or piperazine, each of which is optionally substituted in one to three places;

when —NR[7]A— together with the nitrogen atom forms an unsaturated heterocyclic group, it is imidazole, pyrrole, pyrazole or triazole; and acyl is the acyl residue from a straight-chain or branched aliphatic $C_{1-6}$carboxylic acid, a benzenesulfonic acid which is optionally substituted with halogen or $C_{1-4}$alkyl, or a $C_{1-4}$ alkanesulfonic acid.

10. A compound of claim 1, wherein R[3], R[4], R[7] and R[9] are each hydrogen.

11. A compound of claim 1 wherein R[1] is at the 6-position of the benzoxazine ring.

12. A compound of claim 1, wherein R[8] and B together with the nitrogen atom to which they are bonded form a pyrrolidine-2-thione group.

13. A compound of claim 1, wherein

R[1] is —$(CHR^9)_n$—NR[7]—A—NR[8]—B or —$(CHR^9)_n$—NR[7]—B; or

R[1] and R[2] together form a 5-, 6-, 7- or 8-membered ring which is substituted by —$(CHR^9)_n$—NR[7]—A—NR[5]—B, or —$(CHR^9)_n$—NR[7]—B; and B is: —CR—$(CH_2)_p$—U wherein —$(CH_2)_p$—U is hydrogen, $C_{1-6}$alkyl optionally substituted with halogen, or phenyl optionally substituted with halogen, $C_{1-4}$alkyl, $C_{1-4}$alkoxy or $CF_3$; or —CR—$NR^{15}R^{16}$ wherein R[15] and R[16] are each hydrogen, $C_{1-6}$ alkyl or phenyl; or —$SO_2R^{12}$ in which R[12] is $C_{1-6}$alkyl.

14. A compound of claim 1, wherein R[1] is —$(CHR^9)_r$—NR[7]—$(CH_2)_p$—CR—$(CH_2)_q$—NR[6]—D, or R[1] and R[2] together form a 5-, 6-, 7- or 8-membered ring which is substituted by —$(CHR^9)_r$—NR[7]—$(CH_2)_p$—CR—$(CH_2)_q$—NR[8]—D, and D is hydrogen or a benzyl radical that is optionally substituted with halogen, $C_{1-4}$alkoxy, $CF_3$ or $C_{1-4}$alkyl.

15. A compound of claim 1, wherein R[1] is —$(CHR_9)_r$—NR[7]—$(CH_2)_p$—CR—$(CH_2)_q$—NR[8]—D, or R[1] and R[2] together form a 5-, 6-, 7- or 8-membered ring which is substituted by —$(CHR^9)_r$—NR[7]—$(CH_2)_p$—CR—$(CH_2)_q$—NR[8]—D, and at least one of $(CH_2)_p$ and $(CH_2)_q$ is alkylene of 1–6 carbon atoms.

16. A compound of claim 1, wherein R[3] is —NR[9]—C(=NR[10])—R[11], where R[11] is thienyl.

* * * * *